(12) United States Patent
Schaeffer et al.

(10) Patent No.: US 9,155,641 B2
(45) Date of Patent: Oct. 13, 2015

(54) EXPANDABLE STENT GRAFTS

(75) Inventors: Darin G. Schaeffer, Bloomington, IN (US); David D. Grewe, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1753 days.

(21) Appl. No.: 11/714,058

(22) Filed: Mar. 5, 2007

(65) Prior Publication Data

US 2007/0213805 A1     Sep. 13, 2007

Related U.S. Application Data

(60) Provisional application No. 60/780,894, filed on Mar. 9, 2006.

(51) Int. Cl.
| | | |
|---|---|---|
| A61F 2/07 | (2013.01) | |
| A61F 2/88 | (2006.01) | |
| A61F 2/30 | (2006.01) | |
| A61F 2/915 | (2013.01) | |

(52) U.S. Cl.
CPC . *A61F 2/885* (2013.01); *A61F 2/07* (2013.01); *A61F 2/88* (2013.01); *A61F 2/915* (2013.01); *A61F 2002/075* (2013.01); *A61F 2002/3052* (2013.01); *A61F 2002/30459* (2013.01); *A61F 2002/30461* (2013.01); *A61F 2220/0025* (2013.01); *A61F 2220/0041* (2013.01); *A61F 2220/0066* (2013.01); *A61F 2220/0075* (2013.01)

(58) Field of Classification Search
CPC .............................. A61F 2002/075; A61F 2/07

USPC ..................................... 623/1.13–1.14, 23.7
See application file for complete search history.

(56) References Cited

U.S. PATENT DOCUMENTS

| | | | | |
|---|---|---|---|---|
| 5,507,767 A | * | 4/1996 | Maeda et al. | 623/1.2 |
| 5,637,113 A | * | 6/1997 | Tartaglia et al. | 623/1.42 |
| 5,733,330 A | * | 3/1998 | Cox | 623/1.15 |
| 5,782,904 A | * | 7/1998 | White et al. | 623/1.13 |
| 5,824,037 A | * | 10/1998 | Fogarty et al. | 623/1.13 |
| 5,843,167 A | * | 12/1998 | Dwyer et al. | 623/1.14 |
| 5,876,432 A | | 3/1999 | Lau et al. | |
| 5,925,076 A | * | 7/1999 | Inoue | 606/198 |
| 6,117,166 A | * | 9/2000 | Winston et al. | 623/1.13 |
| 6,331,188 B1 | * | 12/2001 | Lau et al. | 623/1.13 |
| 6,475,232 B1 | * | 11/2002 | Babbs et al. | 623/1.13 |
| 6,592,614 B2 | | 7/2003 | Lenker et al. | |
| 6,605,114 B1 | * | 8/2003 | Yan et al. | 623/1.43 |
| 6,635,081 B2 | | 10/2003 | Khosravi et al. | |
| 6,682,557 B1 | * | 1/2004 | Quiachon et al. | 623/1.35 |
| 6,800,089 B1 | * | 10/2004 | Wang | 623/1.44 |
| 6,805,706 B2 | * | 10/2004 | Solovay et al. | 623/1.15 |
| 6,814,748 B1 | | 11/2004 | Baker et al. | |
| 6,899,728 B1 | * | 5/2005 | Phillips et al. | 623/1.13 |
| 6,939,369 B2 | | 9/2005 | Osborne et al. | |
| 8,998,973 B2 | * | 4/2015 | Molaei et al. | 623/1.15 |
| 2001/0020181 A1 | * | 9/2001 | Layne | 623/1.13 |

(Continued)

FOREIGN PATENT DOCUMENTS

WO        WO 96/21404 A1 * 7/1996 ................ A61F 2/06

*Primary Examiner* — Paul Prebilic
(74) *Attorney, Agent, or Firm* — Brinks Gilson & Lione (57) ABSTRACT

This invention relates to a medical device and, in particular, to a prosthesis or stent graft assembly for use within the human or animal body and, more particularly, to the fastening of a stent to the graft material of the stent graft assembly or prosthesis.

8 Claims, 4 Drawing Sheets

(56) References Cited

U.S. PATENT DOCUMENTS

| | | |
|---|---|---|
| 2004/0030378 A1* | 2/2004 | Khosravi et al. ............. 623/1.13 |
| 2004/0054396 A1 | 3/2004 | Hartley et al. |
| 2004/0073289 A1 | 4/2004 | Hartley |
| 2004/0082989 A1* | 4/2004 | Cook et al. .................. 623/1.13 |
| 2004/0176832 A1 | 9/2004 | Hartley et al. |
| 2004/0225348 A1 | 11/2004 | Case et al. |
| 2005/0131525 A1 | 6/2005 | Hartley |
| 2005/0149167 A1 | 7/2005 | Osborne et al. |

* cited by examiner

EXPANDABLE STENT GRAFTS

RELATED APPLICATIONS

This application claims priority to U.S. provisional application Ser. No. 60/780,894 filed Mar. 9, 2006. The disclosure of this priority application is incorporated herein in its entirety.

TECHNICAL FIELD

This invention relates to a medical device and, in particular, to a prosthesis or stent graft assembly for use within the human or animal body and, more particularly, to the fastening of a stent to a graft material of the stent graft assembly or prosthesis.

BACKGROUND OF THE INVENTION

Various implantable medical devices are advantageously inserted within various body vessels, for example to improve blood flow through a restricted or weakened vessel. Minimally invasive techniques and instruments for placement of intraluminal medical devices have been developed to treat and repair undesirable conditions within body vessels. Various percutaneous methods of implanting medical devices within the body using intraluminal transcatheter delivery systems can be used to treat a variety of conditions. One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Intraluminal medical devices can be deployed in a body vessel at a point of treatment and the delivery device subsequently withdrawn from the vessel, while the medical device retained within the vessel to provide sustained improvement in blood flow or to increase vessel patency.

Stent grafts have proven to be effective medical devices for minimally invasive treatment of vascular occlusions such as atherosclerosis and restenosis and treatment of weakened or diseased vessels. Stent grafts include a graft member inside or outside a stent structure. The graft member reestablishes a flow lumen, the stent structure supports the graft member, reinforces the weakened vessel, and prevents occlusion or stenosis.

It is desirable that there is some secure method for fastening of the stent to the graft member. Examples of fastening of a stent to a graft member are described in commonly owned U.S. Publication No. 2004/0225348, published Nov. 11, 2004 and U.S. Pat. No. 6,939,369 filed Sep. 6, 2005 which are both incorporated by reference. In particular, the method of fastening must be compatible with compressed and expanded states of the stent graft and must allow the graft member to remain fastened to the stent as the device is moved between the compressed and expanded states. For medical devices which move or slide circumferentially, there is a need for a fastening system which allows the support frame to move circumferentially with respect to the graft member such that the graft member and stent remained fastened in and during the transition between the expanded and compressed states and during.

BRIEF SUMMARY

One embodiment of the present invention provides a stent graft assembly, having a tubular graft member, a support frame, and at least one fastener. The graft member is secured to the support frame in a manner that allows the support frame to move circumferentially with respect to the tubular graft member when the support frame is moved between compressed and expanded states.

One embodiment of the present invention provides a stent graft assembly, having a tubular graft member, a support frame, and a means for securing the tubular graft member to the support frame in a manner that permits the support frame to move circumferentially with respect to the tubular graft member when the support frame is moved between compressed and expanded states.

BRIEF DESCRIPTION OF SEVERAL VIEWS OF THE DRAWINGS

Embodiments of the present invention will now be described by way of example with reference to the accompanying drawings.

DETAILED DESCRIPTION OF THE INVENTION

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

An "alloy" is a substance composed of two or more metals or of a metal and a nonmetal united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

A "biodegradable" material is a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial bioabsorption.

As used herein, the phrase "bioactive agent" refers to any pharmaceutically active agent that produces an intended therapeutic effect on the body to treat or prevent conditions or diseases.

Implantable Stent Graft

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are stents.

One aspect of the present invention provides a self-expanding or otherwise expandable stent graft for deployment within a bodily passageway, such as a vessel or duct of a patient. The stent graft is typically delivered and implanted using well-known transcatheter techniques for self-expanding or otherwise expandable prostheses.

The stent graft of the present invention includes a support frame and a graft member. The graft member is positioned coaxially within the inner surface of the support structure or over the outer surface of the support structure. The stent graft, when positioned in an artery, generally conforms to the shape of the artery wall and defines a lumen within the vessel. The stent graft, when positioned in a vein, generally supports the vein and defines a lumen within the vein.

The graft member is slidably secured to the support frame in a manner such that the support frame can move circumferentially with respect to the graft member during radial alteration of the stent.

Illustrative Stent Graft

This invention will be particularly discussed in relation to the fastening of self-expanding stents to graft members, however, it is to be realized that the invention is not limited to this particular application, but may be applicable to other types of stents and other graft members.

Figure 1:
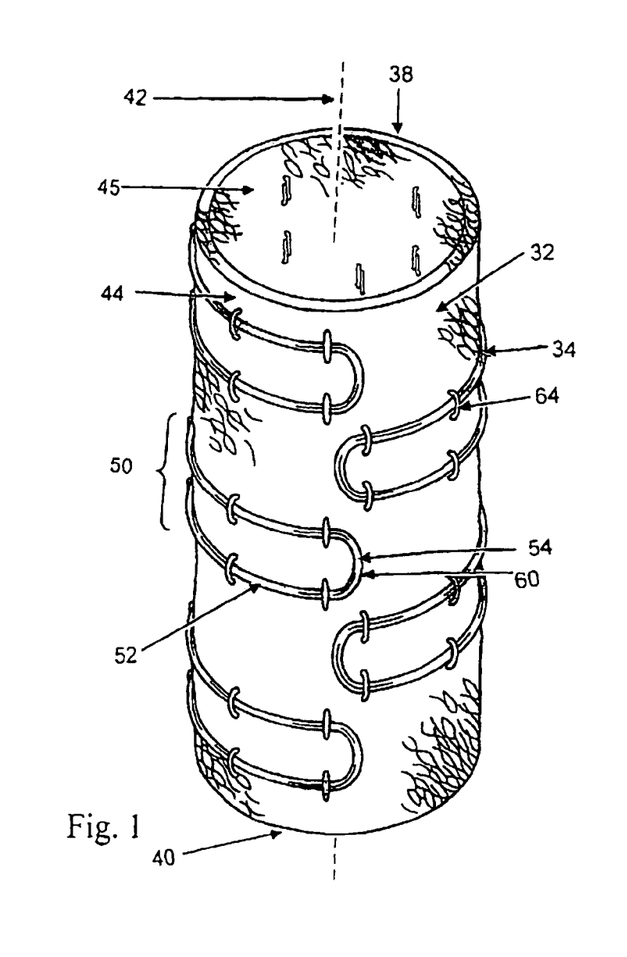
FIG. 1 is a schematic view of an illustrative embodiment of the present invention, depicting a stent graft assembly in a radially expanded state.

FIG. 1 shows an illustrative embodiment of the invention, in which the stent graft assembly is in an expanded state, and includes a graft member 32 with a support frame 34 fastened to the graft member.

The stent graft assembly includes a support frame which has a cylindrical shape coaxially disposed about a longitudinal axis 42, an inner surface, an outer surface, and a plurality of arms 50. The support frame extends both "axially" and "circumferentially" along the longitudinal axis. "Circumferentially" refers the arms 50 being bent into generally circular or elliptical configurations and generally perpendicular to the longitudinal axis. The arms need not extend completely around the circumference, and preferably extend only around a portion of the circumference. "Axially" refers to the arrangement of a plurality of arms extending along the longitudinal axis, each arm being generally perpendicular to the axis. The support frame, when completed, is in a substantially cylindrical or drum form.

The support frame is defined by a plurality of arms, each arm including one or more circumferential segments 52. The circumferential segments are generally perpendicular to the longitudinal axis and extend along the circumference or periphery of the support frame. In one embodiment two circumferential segments are interconnected by a curved segment 54 to form arm with an outermost edge 60.

The stent graft assembly includes a tubular graft member for implanting in a body vessel. The tubular graft member is deformable and has first 38 and second 40 ends defining a longitudinal axis, a peripheral surface 44 and inner surface 45 extending between the first and second ends.

The tubular graft member is attached to the support frame with at least one fastener 64. Each fastener slidably secures an arm or a portion of an arm to the peripheral surface. The arm slidably secured by at least one fastener may slide generally perpendicular to the longitudinal axis and circumferentially with respect to the peripheral surface during radial alteration of the support frame. Radial alteration is the expansion or contraction of the circumferential dimension of the support frame such that the diameter of the support frame is either enlarged or reduced during expansion or contraction, respectively. The graft member is attached to the support frame at a point of attachment on the circumferential segment. The point of attachment is defined as the point on the circumferential segment where the graft member is attached. The point of attachment is represented by the point on the circumferential segment where the fastener contacts, crosses over, or wraps around the circumferential segment. Each fastener has a point of attachment on the circumferential segment, and thus the graft member attached by a plurality of fasteners is attached at multiple points of attachment, defined by multiple fasteners and the position thereof.

Figure 2:
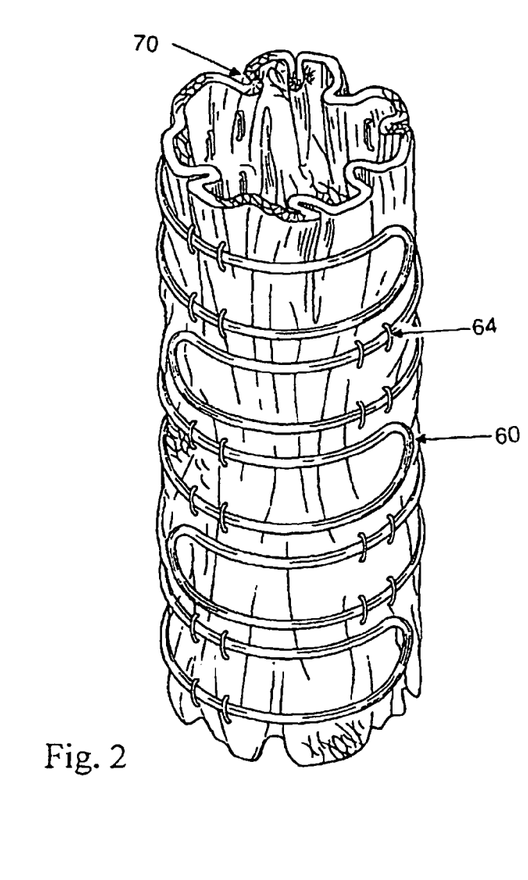
FIG. 2 is another schematic view of an illustrative embodiment of the present invention, depicting a stent graft assembly in a compressed state.

FIG. 2 illustrates a stent graft assembly in a contracted state. During radial alteration, oppositely facing arms move radially and circumferentially relative to each other, and the point of attachment on the circumferential segment moves relative to and along the circumferential segment. During contraction of the stent graft assembly, the oppositely facing arms move in opposite circumferential directions such that the outermost edges of the oppositely facing arms move circumferentially towards and past each other. The point of attachment slides away from outermost edge 60. When a circumferential segment is slidably secured by more than one fastener, the point of each attachment of each fastener on the circumferential segment moves. For example, during contraction of a stent graft assembly, the point of attachments move distally from the outermost edge, causing neighboring points of attachment on a singular circumferential segment to move closer together.

As the point of attachment moves during contraction of the stent graft assembly, the arms of the support frame slide relative to the fasteners and peripheral surface of the graft member, causing the tubular graft member to gather in a series of folds or pleats 70. When the graft member is attached to the inner surface of the support frame, these pleats or folds 70 are formed in lumen defined by the support frame.

The Support Frame

The support frame used in the stent graft assembly of the present invention can be, for example, formed from wire, cut from a sheet or a section of cannula, molded or fabricated from a polymer, biomaterial, or composite material, or a combination thereof. The pattern (i.e., configuration of struts and cells) of the outer frame, which is selected to provide radial expandability to the device is also not critical for an understanding of the invention. Any support frame is applicable for use with the claimed stent graft assembly so long as this frame supports the graft member in the required position, can move between a compressed state and an expanded state and can be slidably secured to the graft member.

Any suitable support frame can be used as the support frame in the medical device. The specific support frame chosen will depend on several considerations, including the size and configuration of the vessel and the size, the nature of the medical device, the vessel in which the medical device is being implanted, the axial length of the treatment site, the inner diameter of the body vessel, the delivery method for placing the support frame, and other factors. Those skilled in the art can determine an appropriate implantable frame based on these and other factors.

The support frame is preferably a substantially cylindrical implantable frame defining a central longitudinal lumen. The support frame preferably defines a substantially cylindrical or elliptical lumen providing a conduit for fluid flow. Preferably the support frame has arms which circumferentially support the graft member and are bent into generally circular or elliptical configurations. The arms have circumferential segments which move circumferentially when the support frame is moved between the compressed state and the expanded state.

Optionally an arm may have one or more curved segments 54. In other embodiments, an arm 50 may contain a plurality of curved segments, no curved segments, or combinations of circumferential and curved segments. Examples of arms that are within the scope of this invention are disclosed in U.S. Pat. No. 6,409,752, the entire disclose of which is hereby incorporated by reference.

In one embodiment, the support frame 34 is configured as a vascular stent such as the commercially available Gianturco-Roubin FLEX-STENT® or GR II™ coronary stent from Cook Incorporated, Bloomington, Ind. Such stents are typically about 10 to about 60 mm in length and designed to expand to a diameter of about 2 to about 6 mm when inserted into the vascular system of the patient. The Gianturco-Roubin stent in particular is typically about 12 to about 25 mm in length and designed to expand to a diameter of about 2 to about 4 mm when so inserted.

These stent dimensions are, of course, applicable to exemplary stents employed in the coronary arteries. Support frames such as stents or catheter portions intended to be employed at other sites in the patient, such as in the aorta, esophagus, trachea, colon, biliary tract, or urinary tract will have different dimensions more suited to such use. For example, aortic, esophageal, tracheal and colonic stents may have diameters up to about 25 mm and lengths about 100 mm or longer.

Figure 3:
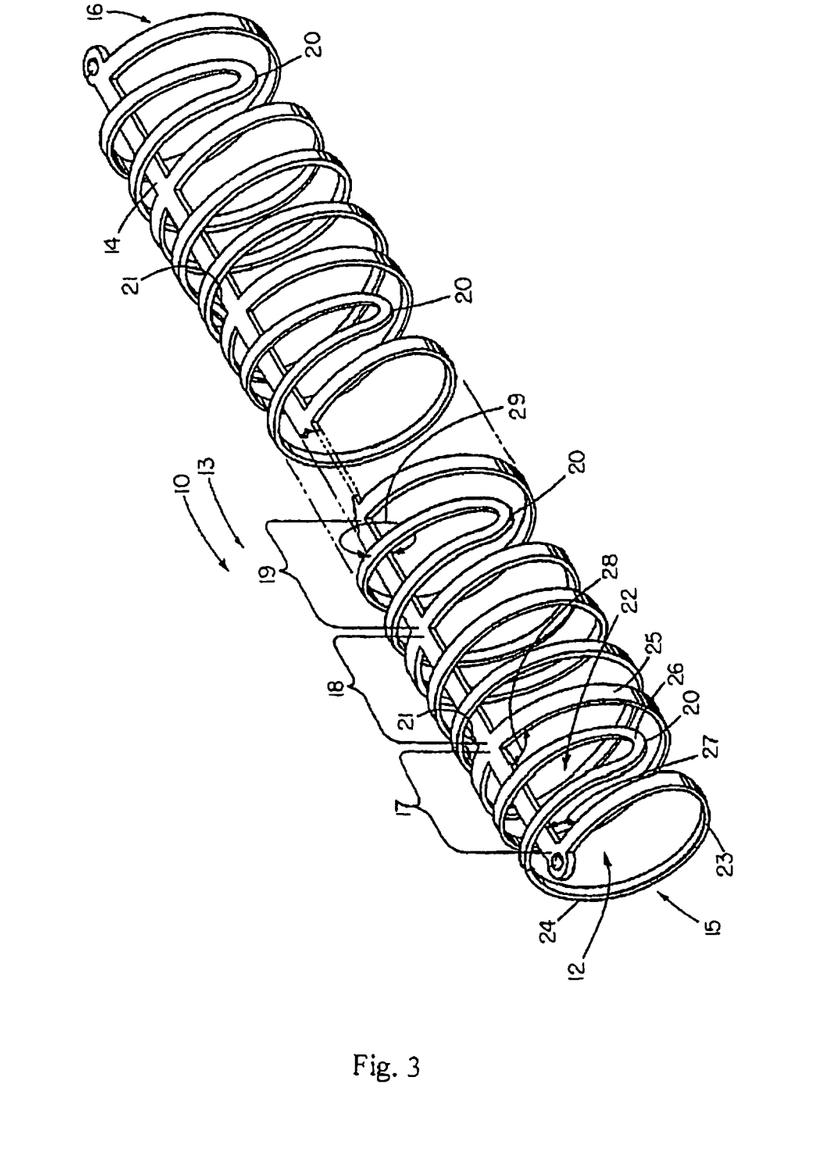
FIG. 3 is a schematic view of an illustrative support frame.

FIG. 3 depicts a pictorial view of an illustrative support frame. The support frame is a GR II™ which is disclosed in U.S. Pat. Nos. 5,632,771 and 6,409,752, the entire disclosures of which are hereby incorporated by reference. Unmounted flexible stent 10 in an overlapping state and comprising a waveform pattern 13 formed from a flat sheet of biocompatible material and into a tubular shape. The tubular shaped pattern is expanded in a body passage such as a blood vessel to maintain an open lumen therethrough. Pattern 13 is formed from a flat sheet of malleable, biocompatible material, for example, photochemically removing a majority of the sheet material and leaving a framework of integrated support members that has a small surface area relative to the initial surface area of the sheet. After formation from the sheet, the pattern is formed into a partially cylindrical or U-shaped surface around a cylindrical mandrel and then positioned in the overlapping state around a delivery device and into tubular shape.

Pattern 13 includes a reinforcing member 14 extending longitudinally between opposite ends 15 and 16 for providing longitudinal stability thereof, particularly during radial expansion of the stent in the body passage. The length of prior art stents that are formed from a tube typically shorten as the stent is radially expanded. When formed into a tubular shape, pattern 13 includes a plurality of interposed closed cells 17-19 that extend laterally from the reinforcing member for providing vessel wall support. The tubular shaped pattern also exhibits longitudinal flexibility for introducing the stent through tortuous vessels to, for example, a coronary artery. Unlike a wire stent in which a wire is bent into a waveform pattern, waveform pattern 13 is formed from a flat sheet of material without any stresses being introduced at the curved segments thereof. As a result, thickness 23 of stent 10, as well as the sheet, can be made extremely thin in comparison to that of a wire stent to minimize endothelial tissue buildup in the vessel. The same well-known moment of inertia or stiffness of a wire stent is maintained by adjusting the width of each pattern member segment for a given sheet thickness.

When stent 10 is positioned in the overlapping state around a delivery device, any segment of a laterally extending cell that overlaps the reinforcing member only forms a combined thickness 29 with and along the reinforcing member of no more than substantially twice the thickness of the sheet material. When the stent is expanded in a blood vessel, the tubular shape is radially altered from a reduced, minimal inside diameter to an expanded diameter for holding the blood vessel open. In addition, oppositely facing, outermost longitudinal edges 20 and 21 of the pattern move radially and circumferentially relative to each other so that the pattern in the sheet of material is not stressed or deformed in the plane of the sheet of material. The substantially cylindrical surface of the tubular shape has a range of diameters between the expanded diameter and the reduced diameter for holding the vessel open in which the interposed cells are free of overlapping sheet material. The pattern is integrated in such a way that the framework thereof maintains a fixed length when the cylindrical surface of the tubular shape is expanded from the reduced diameter of the overlapping state to a larger diameter.

Interposed cell 17 includes fixedly sized aperture 22 with segments 24-26 and reinforcing member 14 disposed around the aperture. Substantially straight segments 24 and 25 extend laterally from reinforcing member 14, and curved segment 26 interconnects straight segments 24 and 25. Straight segments 24 and 25 are positioned circumferentially around the tubular shape in the space of aperture 22 without overlapping themselves or other adjacent cell segments for minimizing the stent profile or thickness in the overlapping state. Straight segments 24 and 25 extend laterally from the reinforcing member at angles 27 and 28, for example, both slightly acute at 82-83 degrees. Therefore, as depicted in FIG. 3, the straight segments cross over reinforcing member 14 but do not overlap themselves or each other. Furthermore, interposed cell 17 is separated from adjacent cells so that the segments of other cells do not overlap segments of cell 17. The width of the segments is greater than the thickness of the segments, or the sheet of biocompatible material, to maintain an acceptable moment of inertia and to increase the effective vessel wall support area. For example, segments 24-26 are approximately 0.014" wide and 0.005" thick.

Figure 4:
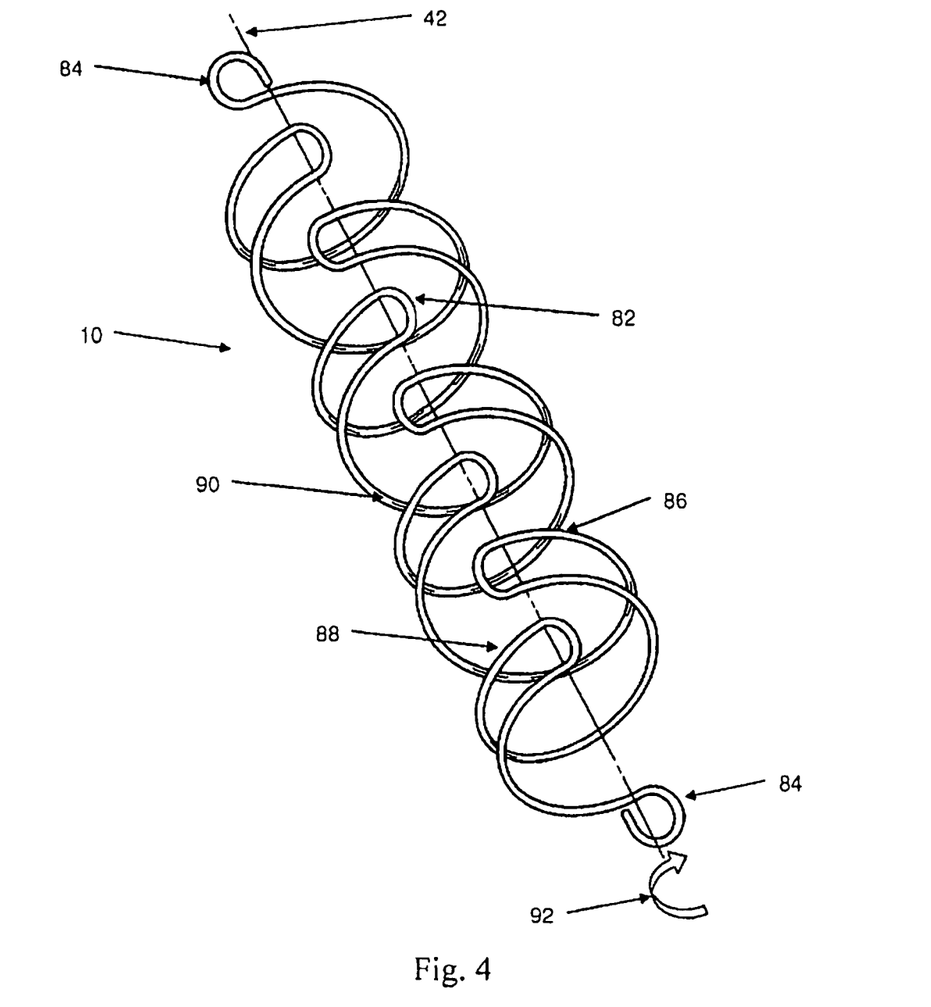
FIG. 4 is a schematic view of another illustrative support frame.

FIG. 4 depicts a pictorial view of an illustrative support frame. The support frame is a Gianturco-Roubin FLEX-STENT® which is disclosed in U.S. Pat. Nos. 4,800,882 and 5,041,126, the entire disclosures of which are hereby incorporated by reference. The unmounted flexible stent 10 is shown as having a longitudinal axis 42. The stent comprises a plurality of curved sections 90 that are situated generally perpendicular to the axis 42. Adjacent curved sections 90 are joined by bends or cusps 82. A loop 84 is formed at each free end of the wire stent 10 in order to shield the wire end. The curved sections 90 are formed into a circular configuration so that the stent 10 has a cylindrical opening formed therein. The curved sections 90 and cusps 82 form a series of alternating clockwise and counter-clockwise loops 88 and 86, respectively. The clockwise direction relative to the axis 42 has been arbitrarily selected and is noted by the heavy arrow 92.

Preferably, the implantable frame is adapted for intraluminal implantation in a body vessel using a catheter delivery system and is moveable between a first, compressed configuration for delivery within the catheter delivery system and a second, expanded configuration upon deployment within the body vessel. In some embodiments, the expanded configurations can be resiliently further extended in one or more radial directions. In some embodiments, a frame can expand from a compressed, or unexpanded, delivery configuration to one or more radially expanded deployment configurations, for example through self-expansion or balloon expansion of the frame. The expanded configuration can have any suitable cross-sectional configuration, including circular or elliptical. In one embodiment, the frame can be oriented along the longitudinal axis of a body vessel in the expanded or compressed configurations.

Preferably, an implantable frame is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration. A self-expanding frame can be sized and configured to exert an outward radial force on a body vessel upon implantation, for example to secure the frame in the body vessel or to exert an outward radial force on the body vessel (for example, to perform a "stenting" function).

Support Frame Composition

The materials used in the support frame, including the outer frame and the radial members can be selected from a well-known list of suitable metals and polymeric materials appropriate for the particular application, depending on necessary characteristics that are required (self-expansion, high radial force, collapsibility, etc.). Suitable metals or metal alloys include: stainless steels (e.g., 316, 316L or 304); nickel-titanium alloys including shape memory or superelastic types (e.g NITINOL or ELASTINITE); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In various embodiments, the support frame comprises a metallic material selected from stainless steel, nickel, silver, platinum, gold, titanium, tantalum, iridium, tungsten, a self-expanding nickel-titanium alloy, NITINOL, or inconel.

One particularly preferred material for forming a frame is a self-expanding material such as the superelastic nickel-titanium alloy sold under the tradename NITINOL. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at below body temperature to insure a rapid transition from the martinsitic state to the austenitic state when the frame can be implanted in a body lumen.

Preferably, the support frame comprises a self-expanding nickel titanium (NiTi) alloy material. The nickel titanium alloy sold under the tradename NITINOL is a suitable self-expanding material that can be deformed by collapsing the frame and creating stress which causes the NiTi to reversibly change to the martensitic phase. The support frame can be restrained in the deformed condition inside a delivery sheath typically to facilitate the insertion into a patient's body, with such deformation causing the isothermal phase transformation. Once within the body lumen, the restraint on the support frame can be removed, thereby reducing the stress thereon so that the superelastic support frame returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

Some embodiments provide support frames that are not self-expanding, or that do not comprise superelastic materials. For example, in other embodiments, the support frame can comprise silicon-carbide (SiC). For example, published U.S. Patent Application No. US2004/034409 to Hueblein et al., published on Feb. 14, 2004 and incorporated in its entirety herein by reference, discloses various suitable frame materials and configurations.

Other suitable materials used in the support frame include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

Graft Materials

The graft member is formed of a graft material which is biocomaptible. Examples of graft materials include polyesters, such as Dacron® (polyethylene terphthalate or PET); fluorinated polymers, such as PTFE (polytetrafluoroethylene) and Teflon® (expanded polytetrafluoroethylene or eP.TFE); polyurethanes such as THORALON™; polyamides such as nylon; or any other suitable material such as coliagenous extracellular matrix (ECM) material including small intestine submucosa (SIS), which is commercially available from Cook Biotech, West Lafayette, Ind., U.S.A. Besides SIS, examples of ECM's include pericardium, stomach submucosa, liver basement membrane, urinary bladder submucosa, tissue mucosa, and dura mater.

Graft materials may include sheets containing a biocompatible polymer. Examples of biocompatible polymers from which sheets can be formed include polyesters, such as polyethylene terephthalate, polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a sheet can be used to make a graft material, provided the final material is biocompatible. Polymers that can be formed into a sheet include polyolefins, polyacrylonitrile, nylons, polyaramids and polysulfones, in addition to polyesters, fluorinated polymers, polysiloxanes and polyurethanes as listed above. Preferably the sheet is made of one or more polymers that do not require treatment or modification to be biocompatible.

The graft material may include a biocompatible polyurethane. Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.). THORALON (THORATEC, Pleasanton, Calif.), is described in U.S. Pat. No. 6,939,377 and U.S. Pat. No. 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664.

Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

Graft materials may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave. A textile material contains fibers and interstices between the fibers.

In one example of woven textiles, knitted textiles include weft knit and warp knit fiber arrays. Weft knit fabric structures (including double-knit structures) utilize interlocked fiber loops in a filling-wise, or weft, direction, while warp knit structures utilize fabric loops interlocked in a length wise, or warp, direction. Weft knit structures generally are more elastic than warp knit structures, but the resiliency of warp knit fabrics is satisfactory to provide a substantial degree of elasticity, or resiliency, to the fabric structure without substantially relying on tensile fiber elongation for such elasticity. Weft knit fabrics generally have two dimensional elasticity (or stretch), while warp knit fabrics generally have unidirectional (width wise) elasticity. The different elasticity properties of the various knit or woven structures may be beneficially adapted to the functional requirement of the particular graft material application. In some cases, where little elasticity is desired, the fabric may be woven to minimize in plane elasticity but yet provide flexibility. For large diameter vascular grafts (6 mm diameter or larger) and various reconstructive fabric applications, polyethylene terephthalate fiber fabric arrays of suitably small fiber size may be utilized as materials for subsequent impregnation with the extracellular collagen matrix. Commercially available woven and knitted fabrics of medical grade Dacron fibers including, single and double velour graft fabrics, stretch Dacron graft fabric and Dacron mesh fabrics, provided the fibers that have suitably small diameter and other properties to provide graft materials in accordance with the present invention. For smaller vascular graft applications (less than 6 mm diameter), and for other applications for which suitable substrates of desired structure are not commercially available, special manufacture may be necessary.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, by Tolliver. Fibers similar to those described are currently being manufactured by the DuPont Company from polyethylene terephthalate (often known as "DACRON™" when manufactured by DuPont), and by other companies from various substances.

The graft material may be a reconstituted or naturally-derived collagenous material. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Fastener Types

Figure 5:
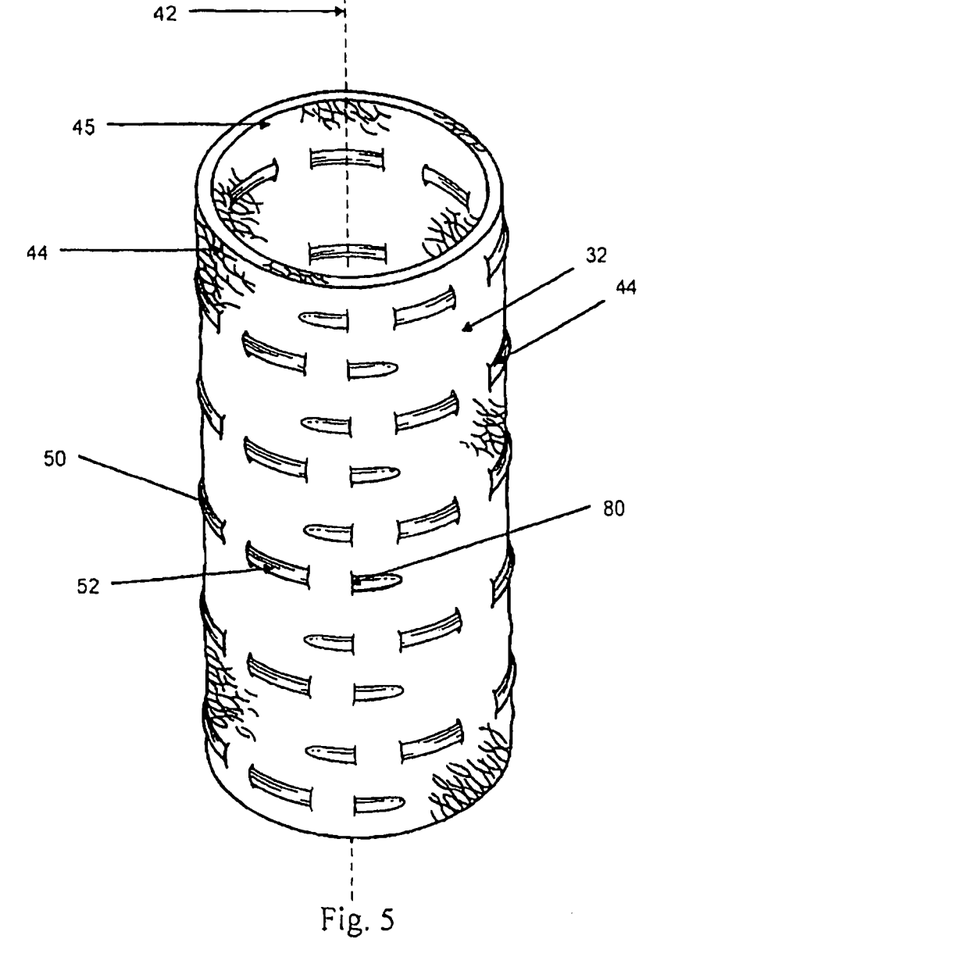
FIG. 5 is a schematic view of an illustrative embodiment of the present invention, depicting a stent graft assembly in a radially expanded state.

In the embodiment illustrated in FIG. 5, the graft member is slidably secured to the support frame by threading the frame through the graft member. Support frame 34 has a plurality of arms 50 which are bent into generally circular or elliptical configurations. The arms have a circumferential segment 52 which is threaded through an opening 80 in the graft member. Optionally, the perimeter of the opening may be reinforced with a rivet, stitching, or other reinforcement means. The circumferential segment is threaded through a plurality of openings circumferentially aligned along the graft member. When threaded, the circumferential segment is alternately located on the peripheral and inner surface of the graft member with each successive opening that is threaded.

In another embodiment, the graft member is slidably secured to the support frame by a plurality of fasteners. The fastener may be any suitable type of fastener which slidably secures the graft member to the support frame. Examples of suitable fastener include sutures, staples, wires, or fibers. The fastener may be mono filament or multi filament including braided filaments. Preferably the fastener may be an elongate flexible fiber or thread such as a mono filament suture material or braided suture.

Sutures, wires, fibers or threads may be utilized in a sewing operation. For example, the fiber, thread, wire or other suitable strand may extend out of the graft member, pass over the circumferential segment, and extend back into the graft member. This process may be repeated such that a suitable strand extends longitudinally along the graft member and fastens a series of circumferential segments. In this manner a new point of attachment is formed with each time the suitable strand extends out of the graft member, passes over the circumferential segment, and extends back into the graft member. In other embodiments the fastener may include one or more turns of a suitable strand, and may include one or more knots to tie off the suitable strand.

Fastener Materials

The fastener material may be made of any appropriate material which is blood compatible or biocompatible and which slidably secures the graft member to the support frame. Although the fastener may be a single or multiple strand wire (platinum, platinum/tungsten, gold, palladium, tantalum, stainless steel, nickel/titanium, etc. or alloys thereof), much preferred is the use of polymeric biocompatible filaments. Synthetic polymers such as polyethylene, polypropylene, polyurethane, polyglycolic acid, polyesters, polyamides, their mixtures, blends, copolymers, mixtures, blends and copolymers are suitable; preferred of this class are polypropylenes such as PROLENE, polyesters such as polyethylene terephthalate including DACRON®, ETHICON and MYLAR® and polyaramids such as KEVLAR, polyfluorocarbons such as polytetrafluoroethylene with and without copolymerized hexafluoropropylene (TEFLON® or GORE-TEX), and porous or nonporous polyurethanes, and polyurethane ureas such as THORALON. Natural materials or materials based on natural sources such as collagen are also suitable.

Bioactives

Medical devices of the present invention can include a bioactive agent. A bioactive agent can be included in any suitable part of the medical device, for example in the support frame and/or the graft member. Selection of the type of bioactive agent, the portions of the medical device comprising the bioactive agent, and the manner of attaching the bioactive agent to the medical device can be chosen to perform a desired therapeutic function upon implantation and, in particular, to achieve controlled release of the bioactive agent.

For example, a therapeutic bioactive agent can be combined with a biocompatible polyurethane, impregnated in an extracellular collagen matrix material, incorporated in the support frame or coated over any portion of the graft member. In one embodiment, the medical device can comprise one or more graft members comprising a bioactive agent coated on the surface of the graft member or impregnated in the graft member. In another aspect, a bioactive material is combined with a biodegradable polymer to form a portion of the support frame.

A bioactive agent can be incorporated in or applied to portions of the graft member by any suitable method that permits controlled release of the bioactive agent material and the effectiveness thereof for an intended purpose upon implantation in the body vessel. The configuration of the bioactive agent on or in the graft member will depend in part on the desired rate of elution for the bioactive agent. Bioactive agents can be coated directly on the graft member surface or can be adhered to a graft member by means of a coating. For example, a bioactive agent can be blended with a polymer and spray or dip coated on the graft member surface. For example, a bioactive agent material can be posited on the surface of the graft member and a porous coating layer can be posited over the bioactive agent material. The bioactive agent material can diffuse through the porous coating layer. Multiple porous coating layers and or pore size can be used to control the rate of diffusion of the bioactive agent material. The coating layer can also be nonporous wherein the rate of diffusion of the bioactive agent material through the coating layer is controlled by the rate of dissolution of the bioactive agent material in the coating layer.

The bioactive agent material can also be dispersed throughout the coating layer, by for example, blending the bioactive agent with the polymer solution that forms the coating layer. If the coating layer is biostable, the bioactive agent can diffuse through the coating layer. If the coating layer is biodegradable, the bioactive agent is released upon erosion of the biodegradable coating layer.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can optionally be applied to or incorporated in any suitable portion of the medical device. The bioactive agent can be applied to or incorporated in the medical device, a polymer coating applied to the medical device, a material attached to the medical device or a material forming at least a portion of the medical device. The bioactive agent can be incorporated within the material forming the support frame, or within pores formed in the surface of the support frame. The medical device can optionally comprise a coating layer containing the bioactive agent, or combinations of multiple coating layers configured to promote a desirable rate of elution of the bioactive from the medical device upon implantation within the body.

A coating layer comprising a bioactive agent can comprise a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the medical device upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Multiple coating layers can be configured to provide a medical device with a desirable bioactive agent elution rate upon implantation. The medical device can comprise a diffusion layer positioned between a portion of the medical device that comprises a bioactive agent and the portion of the medical device contacting the body upon implantation. For example, the diffusion layer can be a porous layer positioned on top of a coating layer that comprises a bioactive agent. The diffusion layer can also be a porous layer positioned on top of a bioactive agent coated on or incorporated within a portion of the medical device.

A porous diffusion layer is preferably configured to permit diffusion of the bioactive agent from the medical device upon implantation within the body at a desirable elution rate. Prior to implantation in the body, the diffusion layer can be substantially free of the bioactive agent. Alternatively, the diffusion layer can comprise a bioactive agent within pores in the diffusion layer. Optionally, the diffusion layer can comprise a mixture of a biodegradable polymer and a bioactive positioned within pores of a biostable polymer of a diffusion layer. In another embodiment, the porous diffusion layer can comprise a mixture of a biodegradable polymer and a biostable polymer, configured to permit absorption of the biodegradable polymer upon implantation of the medical device to form one or more channels in the biostable polymer to permit an underlying bioactive agent to diffuse through the pores formed in the biostable polymer.

In one aspect of the invention, the bioactive agent is an antithrombogenic bioactive agent. Medical devices comprising an antithrombogenic bioactive agent are particularly preferred for implantation in areas of the body that contact blood. An antithrombogenic bioactive agent is any therapeutic agent that inhibits or prevents thrombus formation within a body vessel. The medical device can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis.

Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Other examples of bioactive coating compounds include antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPARα-agonist, a PPARδ-agonist and RXR agonists, as disclosed in published U.S. Patent Application US2004/0073297 to Rohde et al., published on Apr. 15, 2004 and incorporated in its entirety herein by reference.

Methods of Implantation

The medical device as described herein can be delivered to any suitable body vessel, including a vein, artery, biliary duct, ureteral vessel, body passage or portion of the alimentary canal. Methods for delivering a medical device as described herein to any suitable body vessel are also provided, such as a vein, artery, biliary duct, ureteral vessel, body passage or portion of the alimentary canal. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

In some embodiments, medical device of the present invention having a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the medical device.

In one aspect, the medical device described herein are implanted from a portion of a catheter inserted in a body vessel.

Still other embodiments provide methods of treating a subject, which can be animal or human, comprising the step of implanting one or more medical devices as described herein. In some embodiments, methods of treating may also include the step of delivering a medical device to a point of treatment in a body vessel, or deploying a medical device at the point of treatment. Methods for treating certain conditions are also provided, such as, esophageal reflux, restenosis or atherosclerosis.

Treatment

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures.

An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

Treatment of vascular conditions near a branch point with an endoluminal prosthesis can present a number of difficulties. A single, straight section of a tubular prosthesis may not be able to span the aneurysm or dissection and still maintain sufficient contact with healthy vascular tissue to secure the prosthesis and to prevent endoleaks. For example, most abdominal aortic aneurysms occur at or near the iliac bifurcation, and treatment with an endoluminal prosthesis requires the presence of prosthesis material in the main aorta and in the iliac branch arteries (Dietrich, E. B. J. Invasive Cardiol. 13(5): 383-390, 2001). Typically, an endoluminal prosthesis for use near a bifurcation will have a main lumen body, for placement within the aorta, and two branch lumens extending from the main lumen body into the branch arteries.

One example of a bifurcated prosthesis is a single piece prosthesis. Such a unitary structure has a main tubular body and pre-formed leg extensions. The structure provided by this configuration can minimize the probability of leakage within the prosthesis. Another example of a bifurcated prosthesis is a modular system. In this system, one or both of the leg extensions can be attached to a main tubular body to provide the final prosthesis.

Other uses of the stent graft assembly of this invention will be apparent to those of ordinary skill in the art. Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

The invention claimed is:

1. A stent graft assembly comprising:
a tubular graft member having a lumen disposed about a longitudinal axis, the graft member comprising a graft material;
a support frame extending axially and circumferentially around the longitudinal axis, being movable between a compressed state and a radially expanded state; and
at least one fastener that secures the tubular graft member to the support frame in a manner that permits the support frame to move circumferentially with respect to the tubular graft member when the support frame is moved between the compressed state and the expanded state;
wherein the support frame comprises a sheet of biocompatible material having a specified thickness and reinforced with a reinforcing member extending longitudinally therealong and a plurality of cells extending laterally from said reinforcing member in a surface of said sheet of material, selected of said cells being a closed cell and including a fixedly sized aperture extending through said surface of said sheet of material, said sheet of material having a tubular shape including an overlapping state in which certain of said cells overlap said reinforcing member while none of cells overlap each other and form a combined thickness anywhere along said reinforcing member of no more than substantially twice said specified thickness of said sheet of material.

2. The stent graft assembly of claim 1, wherein the graft material is a bioremodelable material.

3. The stent graft assembly of claim 2, wherein the graft material is selected from the group consisting of a reconstituted collagenous material, naturally-derived collagenous material, a collagenous extracellular matrix material, submucosa, renal capsule membrane, dermal collagen, dura mater, pericardium, fascia lata, serosa, peritoneum membrane layers, basement membrane layers, intestinal submucosa, small intestinal submucosa, stomach submucosa, urinary bladder submucosa, and uterine submucosa.

4. The stent graft assembly of claim 1, wherein the graft material comprises an angiogenic collagenous extracellular matrix material.

5. The stent graft assembly of claim 1, wherein the graft material comprises a biocompatible polyurethane.

6. The stent graft assembly of claim 1, further comprising a bioactive material attached to the stent graft assembly.

7. The stent graft assembly of claim 1, wherein the fastener is a suture, loop, staple, wire or fiber.

8. The stent graft assembly of claim 1, wherein the graft material is selected from the group consisting of a biocompatible polyurethane, a reconstituted collagenous material, naturally-derived collagenous material, a collagenous extracellular matrix material, submucosa, renal capsule membrane, dermal collagen, dura mater, pericardium, fascia lata, serosa, peritoneum membranes layers, basement membrane layers, intestinal submucosa, small intestinal submucosa, stomach submucosa, urinary bladder submucosa, and uterine submucosa;

wherein the support frame comprises a nickel-titanium alloy; and wherein the fastener is a suture, loop, staple, wire or fiber.

* * * * *